United States Patent [19]
Soejima

[11] Patent Number: 5,783,267
[45] Date of Patent: Jul. 21, 1998

[54] ARTICLES OF MICROORGANISM-LADEN GLASS AND METHOD OF MANUFACTURING THE SAME

[76] Inventor: Taro Soejima, c/o Soejima Glass Industrial Co., Ltd., 106, Sayanomoto-machi, Saga-shi, Saga-ken, Japan

[21] Appl. No.: 684,744

[22] Filed: Jul. 22, 1996

[30] Foreign Application Priority Data

Jul. 26, 1995 [JP] Japan .................................. 7-211022
Jul. 17, 1996 [JP] Japan .................................. 8-207909

[51] Int. Cl.$^6$ ........................... C04B 33/00; B08B 7/00
[52] U.S. Cl. ........................ 428/34.4; 501/11; 501/32; 501/33
[58] Field of Search ......................... 428/34.4; 501/11, 501/32, 33

[56] References Cited

U.S. PATENT DOCUMENTS

| | | | |
|---|---|---|---|
| 5,061,237 | 10/1991 | Gessler et al. | 604/5 |
| 5,380,439 | 1/1995 | Gilson | 210/615 |
| 5,683,951 | 11/1997 | Higa | 501/141 |

*Primary Examiner*—Charles Nold
*Attorney, Agent, or Firm*—Jones, Tullar & Cooper, P.C.

[57] ABSTRACT

A method for manufacture of glassware with an EM Culture embedded in the glass matrix to improve the palatability of foods or drinks is disclosed. A suitable amount of broth or stock made from fish is mixed with hot water and then a suitable amount of an EM Culture is added to the broth/hot water mixture. The resulting mixture is added to raw materials for glass in a suitable proportion. The mixture is then subjected to aging for a sufficient period of time to have activated the an. EM Culture contained therein. Thereafter, the mixture is melted and formed into a glass article of a desired shape.

2 Claims, No Drawings

ARTICLES OF MICROORGANISM-LADEN GLASS AND METHOD OF MANUFACTURING THE SAME

BACKGROUND OF THE INVENTION

The present invention relates to articles of, microorganism-laden glass such as glassware made of such glass in which the microorganisms embedded in the glass matrix provide certain meritorious effects such as making foods and drinks more palatable, and a method of manufacturing the same.

FIELD OF THE INVENTION

For example, in drinking water, a plurality of water molecules tend to exist in a group (sometimes called "cluster") and it is recognized that breaking up of such clusters of water molecules could lead to improved palatability of the drinking water.

Conventionally, it has been the usual practice to utilize radiation emitted from radium or far infrared rays from certain kinds of heated ceramics to break up clusters of water molecules in the drinking water to thereby make it more palatable, or soft or smooth in taste. Radium is usually added in powder form to raw materials for glass including silica sand, soda ash, limestone and the like, before melting in a furnace. The melted mixture is allowed to cool slowly and then formed to a desired shape by casting, molding, rolling, pressing or other processes. The radiation emanating from radium embedded in the resulting glassware passes through the drinking water held therein, improving the palatability thereof. Unfortunately, such radium-laden glassware is prohibitively expensive because radium is costly.

Recently, a wide variety of microbiological techniques have been developed for use in various fields such as wet refuse treatment, soil amelioration, cleaning of livestock barns, improvement of meat quality, purification of industrial or domestic waste water and the like. One example of such microbiological treatment techniques is to employ a specific culture of effective microorganisms which is commercially available under the tradename of "EM Culture" from Yugengaisha Sanko Sangyo of 259, Miyadaira, Minamikazehara-cho, Okinawa, Japan. It has been recognized by those skilled in the art that the EM Culture can provide a greater resistance to oxdization. The EM Culture can be obtained by culturing aerobic bacteria such as phototrophic or the like in the presence of anaerobic bacteria such as yeast, actinomycetes, lactic acid bacteria or the like. Due to its great oxidation-resistant nature, the EM Culture has been in widespread use as described above.

As a result of extensive and painstaking studies and experiments for additional applications of the EM Culture, it has been discovered this culture lends itself to improving the palatability of foods and drinks. In other words, if the standard glass manufacturing process is modified to add a suitable amount of the EM Culture to the ordinary glass materials before melting, use of a container made of such glass can make foods and drinks more palatable. The glass manufacturing process typically requires a melting temperature much higher than 1000° C., at which temperature it is considered doubtful that microorganisms remain alive. However, surprisingly organoleptic tests have shown significant improvements in the palatability of foods and drinks, although it is not understand scientifically why and how such beneficial results are attained. It has also been discovered that the EM Culture finds utility in hydroponics. A hydroponic tray was fabricated using the EM Culture-laden glass according to the present invention. Comparative tests have shown that the use of the hydroponic tray resulted in vegetables or other plants growing faster than on the ordinary hyrdoponic tray.

A further discovery relates to prolongation of the useful life of a photographic developer. It has been found that glass shapes or glass beads made of the present EM Culture-laden glass, when immersed in a photographic developer, can significantly extend the useful life of the developer.

It would be desirable, and it is an object of the present invention, to provide articles of microorganism-laden glass such as glassware made of such glass that have the above-noted meritorious effects, and a method of manufacturing the same.

SUMMARY OF THE INVENTION

With this object in view, the present invention provides a glass article formed of glass having effective microorganisms embedded in a glass matrix.

The present invention also provides a method for manufacturing a glass article having effective microorganisms embedded in a glass matrix, comprising the steps of: preparing broth or stock made from fish; mixing the broth or stock and hot water in a predetermined proportion to form a first mixture; adding effective microorganisms to the first mixture; subjecting the first mixture to aging for a sufficient period of time to have activated the effective microorganisms contained therein; mixing the first mixture to raw materials for the glass after aging to form a second mixture; melting the second Are; and forming the resulting melt into a glass article of a desired shape.

Further, the present invention provides a method for manufacturing a glass article having effective microorganisms embedded in a glass matrix, comprising the steps of preparing broth or stock made from fish; mixing the broth or stock and hot water in a predetermined proportion to form a first mixture; adding effective microorganisms to the first mixture; mixing the first mixture containing the effective microorganisms to raw materials for the glass to form a second mixture; subjecting the second mixture to aging for a sufficient period of time to have activated the effective microorganisms contained therein; melting the second mire as aged; and forming the resulting melt into a glass article of a desired shape.

The glass articles according to the present invention include glass beads which may vary in size depending upon the specific application. Organoleptic tests have shown that immersion of the glass beads in drinking water, or alcoholic beverages such as distilled liquors including whisky and Japanese spirits called "shochu" and bewares including Japanese "sake", could make them more palatable or soft or smooth in taste. Also, it has been found that placement of the glass beads in a rice cooker in operation could result in the rice being boiled or cooked soft and full.

In addition, it has been discovered that the mocroorganism-laden glass beads according to the present invention have the following advantages:

The glass beads, if immersed in a hot water-filled bathtub, give bathers warm comfort, relaxation and pleasure as obtainable with a hot spring, and also serve to reduce the amount of scale formed in the bathtub.

The glass beads, if immersed in printing ink in an ink fountain of a printing press, can increase the number of sheets to be printed thus reducing the ink cost.

The glass beads, if immersed in a photographic developer, can retard oxidation thereof so that the useful life of the developer may be extended about one and a half times longer than with no such glass beads therein.

The glass beads, if immersed in an automobile fuel tank, can improve fuel consumption and reduce the level of CO and/or NOx emissions in exhaust gas.

The glass beads, if immersed in a hydroponic tray, can provide a faster growth of vegetables or plants.

The above-noted advantages of the glass beads have been experimentally verified and confirmed, although it has thus far not been possible to construct the specific theory underlying the present invention.

DETAILED DESCRIPTION OF THE PREFERRED EMBODIMENTS

The articles of microorganism-laden glass according to the present invention are produced by the following steps:

First, broth or stock made from fish such as a sardine is prepared and a suitable amount of the broth or stock is mixed with hot water while stirring. Thereafter, a suitable amount of the EM Culture is added to the broth/hot water mixture. The resulting mixture is added to raw materials for glass in a suitable proportion and is mixed well until a uniform mixture is formed. The mixture is then subjected to aging for a sufficient period of time to have the EM Culture activated. Thereafter, the mixture is melted and formed into a glass article of a desired shape in accordance with the conventional glass forming process.

The glass articles contemplated by the present invention include glass beads, glassware, glass containers, glass ornaments such as flower vases and goldfish bowls, furniture elements such as glass plates and other shapes.

The glassware formed in accordance with the present invention can provide a more pleasant, softer or smoother taste to beverages including drinking water and alcoholic drinks such as distilled liquors such as whisky, Japanese spirits called "shochu" and bewares such as Japanese "sake". The glass beads placed in a rice cooker also enable the rice to be boiled or cooked soft and full.

The present invention finds many uses, as indicated below:

The glass beads can be immersed in a hot water-filled bathtub to give bathers warm comfort, relaxation and pleasure as obtainable with a hot spring and also to reduce the amount of scale formed in the bathtub. The glass beads can also find utility in the printing art: if the glass beads are immersed in printing ink in an ink fountain of a printing press, the printing press can print a greater number of sheets for a given quantity of the printing ink. Also, if the glass beads are immersed in a photographic developer, they significantly retard the oxidation of the developer and, by so doing, can extend the useful life of the developer, say about one and a half times longer than without the glass beads immersed. Furthermore, the microorganism-laden glass of the present invention has been found to be conducive to improved fuel consumption and reduced CO and/or NOx emissions in automobile. To obtain such advantages, the glass beads are placed in an automobile tank.

EXAMPLE

The present invention will be described by way of example in conjunction with a method for manufacture of the glass beads.

Step 1: 3,300 ml of well water, or city water left to stand for about twenty four hours, is heated to about 42° C.

Step 2: 600 ml of broth or stock made from powdered sardine is added to the heated water while stirring 120 ml of an aqueous solution containing the EM culture is added to the broth/hot water mixture. The aqueous solution contains preferably 1-8 vol %, and more preferably 3 vol %, of EMX. The EMX is commercially available from Yugengaisha Nettaishigen Shokubutsu Kenkyusho of 1212-4 Einohi, Gushicawa-shi Okinawa.

Step 3: The Ore containing the EM culture is uniformly added to preferably 8-15 kg, more preferably 10 kg of a mixture of raw materials for glass including silica sand, soda ash, limestone and colorant.

Step 4: The resulting mixture is loaded into a double-walled bag comprising an outer wall of polyethylene and an inner wall of paper and is subjected to aging for 7-10 days at the room temperature so as to have the EM Culture activated.

Step 5: The mixture thus aged is melted, allowed to cool and formed into various shapes in accordance with the conventional glass forming process. Examples of the shapes include glass beads, glass containers of a suitable size, and glass disks of 10 cm in diameter and 1 cm in thickness.

The container of the EM Culture-laden glass was employed as a hydroponic tray containing a nutrient solution for plants such as young radish plants. A hydroponic tray formed of glass with no EM Culture was provided as a reference. Two groups of young radish plants supported by a sponge were placed in the nutrient solutions in the tray of the EM Culture-laden glass and the reference tray, respectively, for growing under controlled conditions. It was observed, as a result, that the stems of the young radish plants had grown in the hydroponic tray of the present invention about two time faster than in the reference tray in two days. It was found that in four days, the stems of the young radish plants in the hydroponic tray of the present invention had become bigger and about 1.3 times longer than the young radish plants in the reference tray.

Two disks of the EM Culture-laden glass were provided They were immersed in 12 litt. of a photographic developer or developing solution for use in an automatic processor such as Fuji Film Co., Ltd.'s SGX-D1 LD220. During a two-year period from June 1993 to June 1996 when the glass discs were not used, replacement of the spent developer with a fresh one was necessary every 15 days. However, during a one-year period after the use of the glass discs started in June 1995, replacement intervals increased by four days to 19 days. It is considered that the use of the glass disks of the present invention resulted in an extended useful life of the photographic developer.

Although the present invention has been described in detail, it should be understood that various changes, substitutions and alternations may be made herein without departing from the spirit and scope of the present invention as defined by the appended claims. It is to be understood that the terms used in the specification are words of convenience and are not to be construed as limiting terms.

What is claimed is:

1. A glass article formed of glass having an EM culture embedded in a glass matrix.

2. A glass article according to claim 1 characterized in that said glass article is in the form of a container, a disk or a bead.

* * * * *